United States Patent [19]

Edenhofer et al.

[11] 3,985,785

[45] Oct. 12, 1976

[54] CYANOETHYL ACETAMIDINE COMPOUNDS

[75] Inventors: Albrecht Edenhofer, Basel, Switzerland; Hans Spiegelberg-Schoop, deceased, late of Basel, Switzerland; by Annemarie Spiegelberg, heiress, Binningen; by Anna Spiegelberg-Schoop, heiress, Basel, both of Switzerland; Hans Spiegelberg-Von der Crone, heir, La Jolla, Calif.

[73] Assignee: Hoffmann-La Roche Inc., Nutley, N.J.

[22] Filed: Aug. 11, 1975

[21] Appl. No.: 603,843

[30] Foreign Application Priority Data
Aug. 19, 1974 Switzerland.................... 11310/74

[52] U.S. Cl. .................. 260/465.5 R; 260/248 AS; 260/256.4 N
[51] Int. Cl.² ........................................ C07C 121/42
[58] Field of Search ............................ 260/465.5 R

[56] References Cited
OTHER PUBLICATIONS

C.A., 1967–1971 Formula Index, 1973, p. 1277F.
Bruson, "Organic Reactions", vol. 5, 1949, pp. 82–87.

*Primary Examiner*—Joseph Paul Brust
*Attorney, Agent, or Firm*—Samuel L. Welt; Bernard S. Leon; Richard A. Gaither

[57] ABSTRACT

The present invention is related to novel cyano compounds, and a process for their preparation.

4 Claims, No Drawings

CYANOETHYL ACETAMIDINE COMPOUNDS

SUMMARY OF THE INVENTION

This invention is directed to compounds of the formula:

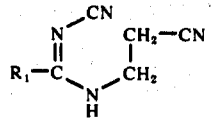   I wherein $R_1$ is lower alkyl.

Another aspect of the invention relates to compounds of the formula:

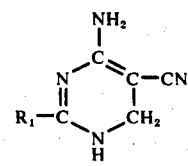   IV wherein $R_1$ is as above; which in turn can be converted by aromatization into compounds of the formula:

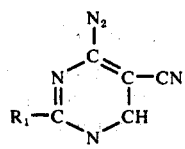   VA wherein $R_1$ is as defined above; or by aromatization with simultaneous reduction into compounds of the formula:

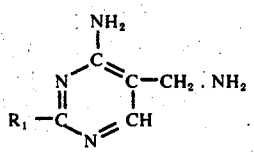   VB wherein $R_1$ is as defined above.

DESCRIPTION OF THE INVENTION

The term "lower alkyl" as used herein comprehends straight and branched chain hydrocarbon groups, having from 1–6 carbon atoms, such as methyl, ethyl, isopropyl or butyl. The term "halogen", as used herein, comprehends fluorine, chlorine, bromine, and iodine, with chlorine being preferred. The term "lower alkanol" comprehends alcohols having straight and branched chain alkyl moieties of 1–6 carbon atoms, such as methanol, ethanol, isopropanol and the like. The term "lower alkoxy", as used herein comprehends alkoxy groups having straight or branched chains of 1–6 carbon atoms such as methoxy, ethoxy, isopropoxy and the like. The term "amino" as employed herein comprehends primary, secondary and tertiary lower alkyl amines having straight or branched chain alkyl groups of 1–6 carbon atoms. The term "aromatic" as used herein comprehends mononuclear aryl groups, such as phenyl which may be unsubstituted or substituted with groups such as amino, lower alkyl, halogen.

The term "alkali or alkali metal", used herein comprehends sodium, potassium and lithium.

Compounds of the formula:

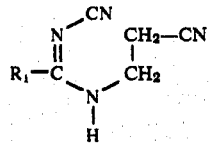   I wherein $R_1$ is as defined above; may be prepared by reacting a compound of the formula:

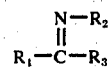   II wherein $R_1$ is as defined above, $R_2$ is hydrogen or cyano and $R_3$ is lower alkoxy, amino, or β-cyanoethylamino; with a compound of the formula:

 $NC-R_4$   III

In which $R_4$ is aminoethyl, vinyl, halogen, or amino.

Compound I is preferably prepared according to one of the following reactions:
 a. N-cyano-acetimino-methyl ether with β-aminopropionitrile,
 b. $N^2$-cyano-acetamidine with acrylonitrile,
 c. $N^1$-(β-cyanoethyl)-acetamidine with cyanamide or the hydrochloride thereof.

The N-cyano-alkaneimino-alkyl ethers and the $N^2$-cyano-alkaneamidines starting materials are known. The $N^1$-(β-cyanoethyl)-alkaneamidines starting material of the formula:

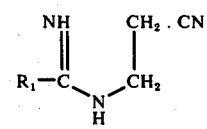   IIa wherein $R_1$ is lower alkyl; are novel and form an additional aspect of this invention. The compounds of formula IIa may be prepared in the same manner as the $N^1$-(β-cyanoethyl)-acetamidine, i.e., by reacting acetiminomethyl ether hydrochloride with β-aminopropionitrile in a lower alkanol at room temperature.

The amidine dinitriles of the formula I may be prepared by reacting the compounds of formula II with the compounds of formula III in a lower alkanol at a temperature ranging from about room temperature to about 40°C.

The compounds of formula I may then be cyclized to form compounds of the formula IV. The cyclization is accomplished by treating the compounds of formula I with a base. Preferred cyclization agents are bases selected from alkali metal, especially lithium and sodium, lower alkyl and aromatic amines bases, such as e.g., N-lithium diethylamine. A particularly preferred cyclization agent is an alkali alkylanilide such as the lithium ethylanilide, especially the sodium methylanilide.

The cyclization is expediently carried out in the presence of an inert solvent such as ethyl ether, isopropyl ether, tetrahydrofuran, dioxane or ethyleneglycol dimethyl ether. The precise reaction conditions are dependent in each case by the particular solvent employed.

The cyclization in ethyl ether, for example, can be carried out in aa Soxhlet apparatus. The cyclization agent is suspended in ether and heated under reflux conditions, the returning condensate eventually dissolving out and bringing the starting material into contact with the cyclization agent. The amount of cyclization agent employed is from about 2–3 moles per mole of starting material.

Tetrahydrofuran, dioxane and ethyleneglycol dimethyl ether are particularly advantageous in that they dissolve the starting compounds as well as the cyclization agent, but the cyclization product which forms is insoluble in the solvent and separates out.

The cyclic compounds of the formula IV that are obtained can be aromatized to form compounds of the formula V by conventional dehydrogenation techniques. Suitable dehydrogenation agents comprise chemical dehydrogenation agents, such as gaseous halogens such as chlorine or alkali ferricynanides, particularly potassium ferricyanide, and oxidizing compounds such as nitrous acid and chromium trioxide. Conventional catalysts such as iron salts, e.g., iron (II) sulfate in conjunction with a peroxide particularly $H_2O_2$ or noble metal catalysts, e.g., palladium-carbon together with oxygen or an oxygen-containing gas, for example, air. Finely divided palladium and platinum may also be used with oxygen or an oxygen-containing gas. Hydrogen peroxide in the presence of a heavy metal salt, especially an iron (II) salt, is particularly preferred from an economic standpoint. Other peroxides that may be employed are di-t-butyl peroxide, dibenzoyl peroxide and the like.

The dehydrogenation can be carried out at about room temperature, generally about 15° C. to about 50° C.

The precise conditions under which the dehydrogenation proceeds will vary, depending upon the dehydrogenation agent chosen. An aqueous solution of sodium nitrite, for example, is added, dropwise, at a temperature around 0° C, to a dilute acetic acid solution of the compound of formula IV. Aqueous hydrogen peroxide is added, dropwise, as a 10% solution at about room temperature into an acetic acid solution of a compound formula IV and an iron (II) salt. The dehydrogenation proceeds particularly smoothly in the presence of potassium ferricyanide in an aqueous medium in a temperature range ranging from about room temperature to about 50° C. Chromium trioxide may be employed at room temperature in the presence of glacial acetic acid. Chlorine gas, when used as a dehydrogenation agent, is generally employed in the presence of catalytic amounts of potassium ferricyanide and is conveniently bubbled into a cold aqueous reaction mixture, said mixture having previously been treated with an alkali carbonate. Finally, the dihydro compound of formula IV can also be dehydrogenated by simply shaking an alcoholic solution thereof under an air supply in the presence of a noble metal catalyst such as palladium-carbon.

The aromatized compounds of the formula VA obtained by dehydrogenation of a compound of the formula IV can be converted in accordance with known hydrogenation procedures, e.g., by catalytic hydrogenation with the aid of palladium-carbon or platinum oxide in acetic acid, into the corresponding diamine of formula VB.

A preferred process for the manufacture of the diamine of the formula VB consists in aromatizing and simultaneously reducing in a single operation the cyano-dihydropyrimidine compound of the formula IV obtained by cyclization of the compound of the formula I. The said two operations are expediently carried out in such a manner that the cyano-dihydropyrimidine compound of the formula IV is hydrogenated with the aid of Raney cobalt in ammonia, optionally under pressure and at elevated temperature.

The novel compounds of the formula I as well as the compounds of the formula IV derived therefrom are intermediates for the preparation of pyrimidine compounds which themselves lead to vitamin $B_1$ and vitamin $B_1$ derivatives.

The following non-limiting examples illustrate the instant invention, all temperatures are in degrees centigrade.

EXAMPLE 1

7.0 g. of β-aminopropionitrile were added dropwise into a solution of 98 g. of N-cyano-acetamino-methyl ether in 200 ml. of isopropanol with stirring and cooling. In so doing, the internal temperature is not allowed to exceed 40° C. The reaction mixture is subsequently stirred for 2 hours at room temperature and cooled to 0° C. The $N^2$-cyano-$N^1$-(β-cyanoethyl)-acetamidine separates out as white crystals and after washing with 50 ml. of cold isopropanol and drying at 50° C. in vacuo, melts at 123°–125° C.

EXAMPLE 2

8.3 g. of $N^1$-cyano-acetamidine were dissolved in 20 ml. of isopropanol. The solution is treated dropwise with 5.3 g. of acrylonitrile with stirring at max. 40° C. The $N^2$-cyano-$N^1$-(β-cyanoethyl)-acetamidine separates from the reaction mixture in the cold as colorless crystals, after washing with 50 ml. of cold isopropanol and subsequent drying at 50° C. in vacuo, melts at 123°–125° C.

EXAMPLE 3

21 g. of cyanamide are dissolved in 120 ml. of abs methanol. The solution is treated at room temperature with 73.5 g. of $N^1$-(β-cyanoethyl)-acetamidine hydrochloride with stirring. The internal temperature is reduced from 40° C. to 20° C. The reaction mixture is stirred for an additional 12 hours at room temperature. The ammonium chloride which is formed is removed by filtration. The filtrate is evaporated under reduced pressure. The remaining $N^2$-cyano-$N^1$-(β-cyanoethyl)-acetamidine melts at 122°–124° C. after recrystallization from isopropanol.

EXAMPLE 4

The $N^1$-(β-cyanoethyl)-acetamidine hydrochloride employed as the starting compound in the previous Example can be prepared as follows:

12.35 g. of acetimino-methyl ether hydrochloride are dissolved in 50 ml. of abs. methanol. The solution is treated dropwise at room temperature with 7.0 g. of β-aminopropionitrile while stirring. After 24 hours, the crude reaction mixture is treated with diethyl ether causing the $N^1$-(β-cyanoethyl)-acetamide to separate out. This crude material can be used without further purification.

EXAMPLE 5

To a suspension of 4.6 g. of powdered sodium in ca 20 ml. of abs. ethyl-benzene dry nitrogen through which dry nitrogen is continuously passed, there is added dropwise over a 2 hour period, with cooling and moderate stirring, a solution of 10.4 g. of monomeric, stabilized styrene and 26.8 g. of N-methylaniline dissolved in 30 ml. of abs. tetrahydrofuran. The temperature is not allowed to exceed 25° C. The yellow solution of sodium methylanilide which forms is stirred for an additional hour at room temperature, then heated to 130° C. under reflux conditions. The reaction mixture is then treated dropwise over a 1 hour period, with intensive stirring, with a solution of 9.0 g. of $N^2$-cyano-$N^1$-($\beta$-cyanoethyl)-acetamidine in 60 ml. of tetrahydrofuran. At the beginning of the addition, a yellow precipitate forms, the color of which increases with intensity as the addition continues. Upon completion of the addition, the reaction mixture is stirred for an additional 2 hours at room temperature. The tetrahydrofuran is subsequently distilled off at about 75° C/200 mmHg with continuation of the stirring and nitrogen passage. The pulpy residue is digested in the nitrogen atmosphere with 50 ml. of ethyl-benzene and then cooled to 0°. The nitrogen passage is discontinued and 100 ml. of ice water is added to the residue with intensive stirring. The temperature is maintained at 5° C. The isolated bright-yellow 4-amino-5-cyano-1,6-dihydro-2-methyl-pyrimidine, after washing with a small amount of ice-water and drying at 60° C. in vacuo, melts at 180°–181° C. (decomp.) and 191° C. after recrystallization from methanol.

EXAMPLE 6

15.6 g. of styrene and 40.2 g. of N-methylaniline are dissolved in 400 ml. of abs ethyl ether and treated with 6.9 g. of finely powdered sodium suspended in 100 ml. of abs. ethyl ether. The mixture is stirred moderate at room temperature under a nitrogen atmosphere. The stirring rate is continuously adjusted such that the sodium powder does not conglomerate. After 15 hours, all but a slight trace of the sodium has dissolved. The reaction vessel is now connected to a Soxhlet apparatus, the housing of which is filled with 13.6 g. of $N^2$-cyano-$N^1$-($\beta$-cyanoethyl)-acetamidine. The flask contents are heated under reflux conditions (bath temperature 80° C.) with intensive stirring, until the acetamidine has been completely removed from the housing and brought into contact with the cyclization agent. The reaction occurs over a 5–6 day period. The weakly yellow-colored sodium comound of the 4-amino-5-cyano-1,6-dihydro-2-methyl-pyrimidine which forms, is decomposed under a nitrogen atmosphere and cooled with 80 ml. of ice-water. In so doing, the reaction temperature of the reaction mixture is maintained at +5° C. The 4-amino-5-cyano-1,6-dihydro-2-methyl-pyrimidine, after washing with ice-water and cold acetone and drying at 50° C. in vacuo, melts at 185° C. (decomp).

EXAMPLE 7

1.36 g. of 4-amino-5-cyano-1,6-dihydro-2-methyl-pyrimidine are dissolved in 10 ml. of a 50% solution of acetic acid and treated with ca 10 mg. of iron (II) sulfate. To this mixture are added dropwise 1.5 ml. of 30% hydrogen peroxide in 4.5 ml. of water in such a manner that the reaction temperature does not exceed 30° C. The oxidation is completed when excess hydrogen peroxide is still detectable 10 minutes after the last addition. The excess hydrogen peroxide is decomposed with sodium bisulfate. The reaction mixture is subsequently adjusted to a pH of 6 by the addition of concentrated sodium hydroxide with cooling and stirring. The isolated 4-amino-5-cyano-2-methyl-pyrimidine, after washing with a small amount of ice-water and recrystallization from water with addition of decolorizing carbon, melts at 257°–258° C.

EXAMPLE 8

1.0 g. of sodium nitrite in 2 ml. of water is added dropwise to a solution of 2.72 g. of 4-amino-5-cyano-1,6-dihydro-2-methyl-pyrimidine in 20 ml. of 50% acetic acid with stirring and cooling. In so doing, the internal temperature should not exceed 10° C. The reaction mixture is stirred for an additional hour at 10° C., then neutralized by the addition of concentrated sodium hydroxide with cooling. The separated 4-amino-5-cyano-2-methyl-pyrimidine, after washing and recrystallization from water, with addition of decolorizing carbon, melts at 257°–258° C.

EXAMPLE 9

13.6 g. of 4-amino-5-cyano-1,6-dihydro-2-methyl-pyrimidine are gradually introduced into a preheated solution (40° C.) of 68 g. of potassium ferricyanide and 14 g. of potassium carbonate in 250 ml. of water. In so doing, the temperature should not exceed 50° C. The mixture is stirred for a further 20 minutes at this temperature. The isolated 4-amino-5-cyano-2-methyl-pyrimidine, after washing with a small amount of ice-water and drying at 90° C. in vacuo, melts at 260°–262° C.

EXAMPLE 10

6.8 g. of 4-amino-5-cyano-1,6-dihydro-2-methyl-pyrimidine are dissolved in 140 ml. of methanol and, 0.7 g. of 5% palladium-carbon are added thereto. This mixture is shaken in an open flask for 90 hours. After separation of the catalyst, the reaction solution is evaporated under reduced pressure. The isolated 4-amino-5-cyano-2-methyl-pyrimidine, melts at 256°–258° C. after recrystallization from water.

EXAMPLE 11

0.7 g. of 4-amino-5-cyano-1,6-dihydro-2-methyl-pyrimidine is dissolved in 3 ml. of glacial acetic acid and subsequently treated with 0.35 g. of chromium trioxide with stirring. All the reactants are solubilized upon warming. A thick colorless slurry results. The slurry is diluted with 100 ml. of water and neutralized with concentrated sodium hydroxide with cooling. The isolated 4-amino-5-cyano-2-methyl-pyrimidine melts at 257°–258° C. after washing with a small amount of water.

EXAMPLE 12

1.6 g. of potassium carbonate and 0.1 g. of potassium ferricyanide are added to a suspension of 1.35 g. of 4-amino-5-cyano-1,6-dihydro-2-methyl-pyrimidine in 25 ml. of water. A moderately strong stream of chlorine gas is bubbled through the mixture, which has been cooled to 10° C. with stirring. Initially, all the reactants are dissolved. Subsequently, a precipitate forms. The reaction is completed when excess chlorine is detectable. The reaction normally takes 3 hours. The 4-amino-5-cyano-2-methyl-pyrimidine obtained after re-precipitation from dilute sulfuric acid/dilute sodium hydroxide, has a melting point of 258°–259° C.

It is claimed:

1. A compound of the formula:
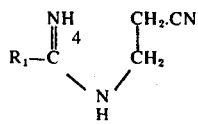
IIa
wherein $R_1$ is lower alkyl having 1–6 carbon atoms.
2. The compound of claim 1 wherein said compound is $N^1$-($\beta$-cyanoethyl)-acetamidine.
3. A compound of the formula:
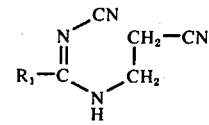
I
wherein $R_1$ is lower alkyl having 1–6 carbon atoms.
4. The compound of claim 3 wherein said compound is $N^2$-cyano-$N^1$-($\beta$-cyanoethyl)-acetamidine.
* * * * *